United States Patent [19]

Matsuoka

[11] Patent Number: 5,386,056

[45] Date of Patent: Jan. 31, 1995

[54] PROCESS FOR PRODUCING 2-HYDROXY-4-METHYLTHIOBUTANOIC ACID

[75] Inventor: Kazuyuki Matsuoka, Kanmakicho, Japan

[73] Assignee: Daicel Chemical Industries, Ltd., Osaka, Japan

[21] Appl. No.: 178,315

[22] PCT Filed: May 20, 1993

[86] PCT No.: PCT/JP93/00659

§ 371 Date: Jan. 12, 1994

§ 102(e) Date: Jan. 12, 1994

[87] PCT Pub. No.: WO93/23372

PCT Pub. Date: Nov. 25, 1993

[30] Foreign Application Priority Data

May 21, 1992 [JP] Japan .................. 4-155802

[51] Int. Cl.$^6$ .................. C07C 323/52; C07C 319/00
[52] U.S. Cl. .................. 562/526; 562/581
[58] Field of Search .................. 562/526, 581

[56] References Cited

U.S. PATENT DOCUMENTS

| | | | |
|---|---|---|---|
| 4,451,486 | 5/1984 | Baker et al. | 424/317 |
| 4,524,077 | 6/1985 | Ruest et al. | 562/581 X |
| 4,855,495 | 8/1989 | Takano | 562/581 |
| 4,912,257 | 3/1990 | Hernandez et al. | 562/581 |

FOREIGN PATENT DOCUMENTS

| | | |
|---|---|---|
| 143100 | 5/1985 | European Pat. Off. . |
| 46-7925 | 2/1971 | Japan . |
| 62-28943 | 6/1987 | Japan . |
| 1290653 | 11/1989 | Japan . |
| 2235846 | 9/1990 | Japan . |
| 2044755 | 10/1980 | United Kingdom . |

*Primary Examiner*—Arthur C. Prescott
*Attorney, Agent, or Firm*—Cushman Darby & Cushman

[57] ABSTRACT

Methyl 2-hydroxy-4-methylthiobutanoate and formamide are produced by means of reacting 2-hydroxy-4-methylthiobutanamide obtained by hydration of 2-hydroxy-4-methylthiobutyronitrile with methyl formate. Said methyl 2-hydroxy-4-methylthiobutanoate is hydrolyzed to give 2-hydroxy-4-methylthiobutanoic acid and methanol. No sulfuric acid is employed as a reacting agent, hence exhaustion of a large quantity of ammonium sulfate is prevented. Formamide and methanol thus produced can be recycled as reactants.

13 Claims, No Drawings

PROCESS FOR PRODUCING 2-HYDROXY-4-METHYLTHIOBUTANOIC ACID

TECHNICAL FIELD

The present invention relates to a process for producing 2-hydroxy-4-methylthiobutanoic acid, which is useful as a feed additive for livestock, for instance.

BACKGROUND ART

A process is known for the production of 2-hydroxy-4-methylthiobutanoic acid which comprises preparing 2-hydroxy-4-methylthiobutyronitrile from acrolein, methanethiol and hydrogen cyanide and hydrating said 2-hydroxy-4-methylthiobutyronitrile in the presence of an excess of sulfuric acid. Since the reactions involved therein can be conducted in a relatively easy manner and give the product in high yields, this process is in use on a commercial scale.

However, the process mentioned above produces waste sulfuric acid and ammonium sulfate in large amounts. Treatment steps for these by-products are thus necessary and much energy is expended in such steps, hence the cost of production of 2-hydroxy-4-methylthiobutanoic acid increases. Discharging large amounts of ammonium sulfate or any other sulfate salt into the natural world is undesirable from the view-point of environmental protection.

Accordingly, it is an object of the invention to provide a process for producing 2-hydroxy-4-methylthiobutanoic acid efficiently and at low cost without causing formation of large amounts of waste.

The following publications may be cited as other prior art with reference to the present invention. Japanese Patent Publication No. 7925/1971 discloses a method of producing 2-hydroxy-4-methylthiobutyronitrile from acrolein cyanohydrin. Japanese Patent Publication No. 28943/1987 discloses a method of producing carboxylic acid esters by reacting a formate ester with a carboxylic acid amide. Japanese Patent Laid-open No. 290653/1989 discloses a method of producing methyl methacrylate using acetone and methyl formate as starting materials. Further, Japanese Patent Laid-open No. 235846/1990 discloses a method of producing methyl formate by dehydrogenating methanol.

However, in these publications is not disclosed a process for producing 2-hydroxy-4-methylthiobutanoic acid which comprises hydrating 2-hydroxy-4-methylthiobutyronitrile, allowing the resulting 2-hydroxy-4-methylthiobutanamide to react with methyl formate to form methyl 2-hydroxy-4-methylthiobutanoate, and hydrolyzing said methyl 2-hydroxy-4-methylthiobutanoate to form 2-hydroxy-4-methylthiobutanoic acid.

DISCLOSURE OF THE INVENTION

The present inventor made intensive investigations to achieve the above object and, as a result, found that 2-hydroxy-4-methylthiobutanoic acid can be obtained very efficiently without causing formation of large amounts of waste when 2-hydroxy-4-methylthiobutyronitrile is hydrated, the resulting 2-hydroxy-4-methylthiobutanamide is then reacted with methyl formate and the thus-formed methyl 2-hydroxy-4-methylthiobutanoate is further subjected to hydrolysis, whereby by-product recycling becomes possible and the use of sulfuric acid is substantially avoided. Based on this finding, the present invention has been completed.

The present invention thus provides a process for producing 2-hydroxy-4-methylthiobutanoic acid which comprises (1) the first step of hydrating 2-hydroxy-4-methylthiobutyronitrile for the formation of 2-hydroxy-4-methylthiobutanamide, (2) the second step of reacting the 2-hydroxy-4-methylthiobutanamide obtained in said first step with methyl formate for the formation of methyl 2-hydroxy-4-methylthiobutanoate and formamide and (3) the third step of hydrolyzing the methyl 2-hydroxy-4-methylthiobutanoate obtained in said second step for the formation of 2-hydroxy-4-methylthiobutanoic acid and methanol.

Hydrogen cyanide obtained by dehydrating said formamide can be utilized as a raw material for said 2-hydroxy-4-methylthiobutyronitrile.

DETAILED DESCRIPTION OF THE INVENTION

A reaction scheme in the process of the present invention is shown as follows, for instance.

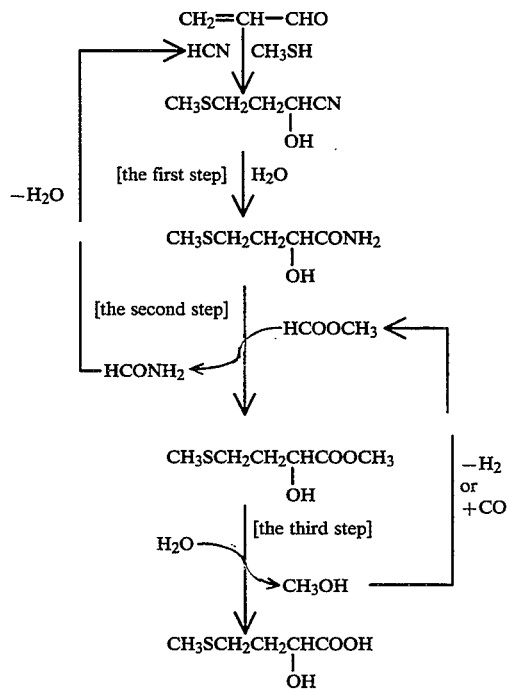

2-Hydroxy-4-methylthiobutyronitrile to be used as the starting material in the first step mentioned above can be produced by a conventional method from hydrogen cyanide, acrolein and methanethiol.

Thus, for instance, acrolein is reacted with methanethiol in the presence of a catalyst to give 3-methylthiopropionaldehyde. As said catalyst, there may be mentioned, for example, alkali metal alkoxides such as sodium methoxide, acetate salts such as copper acetate and cobalt acetate, and organic bases such as pyridine, piperidine and triethylamine.

The thus-obtained 3-methylthiopropionaldehyde is then reacted with hydrogen cyanide in the presence of a catalyst, whereby 2-hydroxy-4-methylthiobutyronitrile can easily be obtained in high yields. As the catalyst, there may be mentioned, for example, alkali metal hydroxides such as sodium hydroxide, alkali metal carbonates such as sodium carbonate, alkali metal hydrogencarbonates such as sodium hydrogencarbonate, alkali metal sulfites such as sodium sulfite, alkali metal hydrogensulfites such as sodium hydrogensulfite, and organic bases such as pyridine and triethylamine.

It is also possible to prepare 2-hydroxy-4-methylthiobutyronitrile by reacting acrolein with hydrogen cyanide and then reacting the resulting acrolein cyanohydrin with methanethiol. Furthermore, it is possible to produce said 2-hydroxy-4-methylthiobutyronitrile by reacting acrolein with hydrogen cyanide and methanethiol in one step in the presence of a catalyst such as ammonium carbonate.

The hydration reaction in the first step mentioned above can be effected by contacting 2-hydroxy-4-methylthiobutyronitrile with water in the presence of a catalyst.

As said catalyst, there may be mentioned catalysts effective for hydration of nitriles, for example strong acids such as sulfuric acid, weak bases such as alkali metal salts or alkaline earth metal salts of weak acids, metals such as manganese, copper and nickel, and oxides of such metals. As the weak base, there may be mentioned, for example, alkali metal borate such as sodium tetraborate, potassium tetraborate, sodium metaborate and potassium metaborate; alkaline earth metal borate such as magnesium orthoborate; alkali metal phosphate such as lithium phosphate, sodium phosphate and potassium phosphate; alkaline earth metal phosphate such as magnesium phosphate and calcium phosphate; alkali metal silicate such as sodium silicate; alkaline earth metal silicate such as calcium silicate; alkali metal salt of carbonic acid such as sodium carbonate, potassium carbonate and sodium hydrogencarbonate; alkaline earth metal carbonate such as magnesium carbonate and calcium carbonate. Among them, weak bases such as alkali metal borate, for example sodium tetraborate, and metal oxides such as manganese oxide are preferred. Even if sulfuric acid is used, the amount thereof required is very small and, therefore, the process remains substantially free from ammonium sulfate formation. This is very advantageous from the commercial viewpoint.

The amount of water to be used in the above hydration reaction is not critical. Generally, however, water is used in an amount of about 0.1 to 300 moles, and preferably about 1 to 150 moles, per mole of 2-hydroxy-4-methylthiobutyronitrile. For promoting smooth progress of the reaction, a water-soluble organic solvent such as acetone or methanol may be added to the reaction system.

The reaction temperature is generally about 20° C. to 150° C., preferably about 40° C. to 120° C. The reaction time may be varied depending on the catalyst employed and the reaction temperature but, generally, about 0.4 to 12 hours is sufficient for the reaction. If the reaction temperature is too high, or the reaction time is too long, part of the product 2-hydroxy-4-methylthiobutanamide may further react with water to give 2-hydroxy-4-methylthiobutanoic acid and/or give a polymeric by-product, so that the yield of the intended product tends to decrease.

The reaction mixture may be submitted, as such, to the second step or, when necessary, subjected to a conventional separation procedure for the separation and recovery of the product 2-hydroxy-4-methylthiobutanamide. The thus-recovered 2-hydroxy-4-methylthiobutanamide is submitted to the second step.

The reaction of 2-hydroxy-4-methylthiobutanamide with methyl formate in the second step is generally carried out in the presence of a catalyst although said reaction may be effected by heating, for example, at about 100° C. to 300° C. in the absence of any catalyst.

Examples of the catalyst mentioned above are mineral acids such as hydrochloric acid, sulfuric acid and nitric acid, alkalis such as sodium hydroxide, metal salts such as copper acetate, manganese naphthenate, aluminum chloride, lead nitrate and iron acetyl-acetonate, metal alkoxides such as sodium methoxide, sodium ethoxide, sodium butoxide, titanium tetraisopropoxide, titanium tetrabutoxide and aluminium tetraisopropoxide, and solid acids such as silica, zeolite and solid phosphoric acid. Among them, metal salts such as copper acetate and metal alkoxides such as sodium methoxide are preferably used.

For producing methyl 2-hydroxy-4-methylthiobutanoate in high yields, it is preferable to use methyl formate in an amount not less than the stoichiometric amount, preferably about 1 to 20 times, more preferably about 1 to 8 times the stoichiometric amount, since the reaction between 2-hydroxy-4-methylthiobutanamide and methyl formate is an equilibrium reaction. Methyl formate may be used also as a solvent.

The reaction mentioned above is preferably carried out in the presence of a solvent so that the reaction can proceed smoothly, although it may be carried out in the absence of any solvent. Said solvent is not limited to any specific species as far as being inert to the reaction, for example an aromatic hydrocarbon such as benzene, toluene, xylene or ethylbenzene, an aliphatic hydrocarbon such as pentane, hexane, heptane or octane, an alicyclic hydrocarbon such as cyclohexane or methylcyclohexane, acetone, methanol or the like. Among them, those solvents in which the reactants are readily soluble, for example methanol, acetone and the like, in particular methanol and the like, are preferred.

The reaction is generally carried out at about 0° C. to 250° C., preferably about 20° C. to 100° C., although the reaction temperature may be varied depending on the catalyst employed, the amount thereof and other factors. The reaction time may be selected according to the rate of reaction, generally within the range of about 0.1 to 6 hours.

When necessary, the products methyl 2-hydroxy-4-methylthiobutanoate and formamide and the unreacted starting materials can be separated and recovered by subjecting the reaction mixture to a conventional separation procedure. In most instances, the separation and recovery can be achieved by such a simple and easy procedure as distillation.

The above-mentioned methyl 2-hydroxy-4-methylthiobutanoate is submitted to the next third step while the unreacted methyl formate and the other can be recycled as the raw materials for the second step mentioned above.

In a preferred embodiment of the present invention, the formamide formed in the second step as a by-product is converted to hydrogen cyanide by dehydration and the hydrogen cyanide is utilized as a raw material for producing 2-hydroxy-4-methylthiobutyronitrile for use in the first step.

The above-mentioned dehydration of formamide can be performed in the manner of a gaseous-phase catalytic reaction in the presence of a dehydration catalyst, for example a conventional solid catalyst such as alumina, silica-alumina, iron-silica, iron phosphate or aluminum phosphate. The reaction temperature is generally about 200° C. to 600° C., preferably about 300° C. to 550° C. The reaction proceeds almost quantitatively.

The hydrolysis of methyl 2-hydroxy-4-methylthiobutanoate in the third step mentioned above is preferably carried out in the manner of acid hydrolysis using an acid catalyst although said hydrolysis can be conducted in the manner of alkali hydrolysis. When acid hydrolysis is employed, waste discharge, for example salt discharge, is minimal and, in addition, such side reactions as polymerization and dehydration are inhibited to a remarkable extent.

As the acid catalyst mentioned above, there may be mentioned mineral acids such as sulfuric acid and hydrochloric acid; sulfonic acids such as benzenesulfonic acid, p-toluenesulfonic acid and naphthalenesulfonic acid; cation exchange resins; and so on. Among them, the cation exchange resins, preferably strongly acidic cation exchange resins, more preferably porous, strongly acidic cation exchange resins, are preferred since they can be readily separated and recovered. As said porous, strongly acidic cation exchange resins, there may be mentioned, for example, Amberlyst 15, Amberlite 200 (both available from Rohm and Haas Co.) and Diaion HPK (available from Mitsubishi Kasei Co., Ltd.).

Since the hydrolysis reaction mentioned above is an equilibrium reaction, water is used preferably in an amount not less than the stoichiometric amount, more preferably about 1 to 100 times the stoichiometric amount, so that 2-hydroxy-4-methylthiobutanoic acid can be obtained in high yields.

The reaction is generally carried out at a temperature of about 0° C. to 100° C., preferably about 20° C. to 200° C., and more preferably about 50° C. to 100° C., although the reaction-temperature may be varied depending on the catalyst employed and the amount thereof. The reaction time can suitably be selected according to the rate of reaction, generally within the range of about 0.5 to 12 hours. The reaction progresses substantially quantitatively.

After completion of the reaction, the reaction mixture is subjected to a conventional separation procedure, as necessary, whereby the desired product 2-hydroxy-4-methylthiobutanoic acid can be separated and recovered.

In a preferred embodiment of the invention, the methanol formed as a by-product in the third step is converted to methyl formate by dehydrogenation or by carbonylation with carbon monoxide, for instance, and the methyl formate can be utilized as a raw material in the second step mentioned above.

The above-mentioned dehydrogenation of methanol can be carried out, for instance, in the manner of gaseous-phase catalytic reaction in the presence of a dehydrogenation catalyst, for example a solid catalyst such as copper oxide-zinc oxide-aluminum oxide or copper chromite. The reaction temperature is generally about 100° C. to 500° C., preferably about 100° C. to 400° C.

The above-mentioned carbonylation of methanol can preferably be carried out in the presence of a catalyst such as a metal alkoxide.

Thus, in accordance with the invention, the use of sulfuric acid as a reactant can be eliminated, so that the discharge of large amounts of waste sulfuric acid or ammonium sulfate can be avoided and the treatment steps for these become unnecessary. Furthermore, since the formamide formed as a by-product in the second step of the process of the invention can be used as a raw material for the production of 2-hydroxy-4-methylthiobutyronitrile for use in the first step and the methanol formed as a by-product in the third step can be utilized as a raw material for the production of methyl formate for use in the second step, the carbon and nitrogen yields are high and the desired compound 2-hydroxy-4-methylthiobutanoic acid can be produced very efficiently.

INDUSTRIAL APPLICABILITY

The product 2-hydroxy-4-methylthiobutanoic acid obtained by the process of the present invention can be used as a feed additive for livestock, for instance.

The following examples illustrate the invention in further detail but are by no means limitative of the scope of the invention.

EXAMPLES

Example

[Production of 2-hydroxy-4-methylthiobutyronitrile]

In a 2-liter flask equipped with a stirrer and a thermometer, were placed 280 g of acrolein, 1 g of hydroquinone and 2.2 g of copper acetate. To the mixture was added dropwise 280 g of methanethiol in one hour with stirring, while the reaction temperature was maintained at 20° C. The reaction mixture was stirred still for one hour, then unreacted methanethiol was distilled off under reduced pressure to give 464 g of 3-methylthiopropionaldehyde (yield: 88.5%).

In a 2-liter flask equipped with a stirrer, a thermometer and a dropping funnel, were placed 208 g of 3-methylthiopropionaldehyde thus obtained, 800 g of methanol and 0.05 g of sodium hydroxide. To the mixture, 59.5 g of hydrogen cyanide was added dropwise in 20 minutes with stirring, while the reaction temperature was maintained at 20° C. The reaction mixture was sill stirred for 2 hours at 20° C., and 50% aqueous solution of sulfuric acid was added to the reaction mixture to adjust to pH 3. Unreacted hydrogen cyanide was distilled off under reduced pressure to give 255 g of 2-hydroxy-4-methylthiobutyronitrile (yield: 96.1%).

[Production of 2-hydroxy-4-methylthiobutanamide (the first step) (1)]

In a 2-liter flask equipped with a stirrer, a thermometer and a reflux condenser, were placed 197 g of 2-hydroxy-4-methylthiobutyronitrile thus obtained in the above mentioned step, 450 g of water, 150 g of acetone and 65 g of manganese dioxide. The mixture was stirred for 6 hours at 60° C. After cooling the reaction mixture, the catalyst was removed off by suction-filtration. The filtrate was concentrated under reduced pressure, and the resulting solid was recrystallized from acetone to give 199 g of 2-hydroxy-4-methylthiobutanamide (yield: 89.0%), mp 98° C.

[Production of 2-hydroxy-4-methylthiobutanamide (the first step) (2)]

In a 2-liter flask equipped with a stirrer, a thermometer and a reflux condenser, 49.3 g of 2-hydroxy-4-methylthiobutyronitrile thus obtained in the above mentioned step, 750 g of water and 15 g of sodium tetraborate were stirred for 2 hours at 75° C. The reaction mixture was concentrated under reduced pressure, and the resulting solid was recrystallized from acetone to give 44.2 g of 2-hydroxy-4-methylthiobutanamide (yield: 79.2%), mp 98.5° C.

[Production of methyl 2-hydroxy-4-methylthiobutanoate (the second step)]

In an autoclave equipped with a stirrer, were placed 224 g of 2-hydroxy-4-methylthiobutanamide obtained in the above mentioned step, 450 g of methyl formate, 240 g of methanol and 1.2 g of sodium methoxide, and the mixture was stirred for 2 hours at 60° C.

As the result of analysis of the reaction mixture, the conversion rate of 2-hydroxy-4-methylthiobutanamide was 64%, the selectivity for methyl 2-hydroxy-4-methylthiobutanoate was 91.5% and the selectivity for formamide was 86.4%, based on 2-hydroxy-4-methylthiobutanamide respectively.

Sodium methoxide in the reaction mixture was neutralized with hydrochloric acid and the resultant was distilled in a conventional manner to give 141 g of methyl 2-hydroxy-4-methylthiobutanoate and 35.3 g of formamide.

[Production of 2-hydroxy-4-methylthiobutanoic acid (the third step)]

To 131 g of methyl 2-hydroxy-4-methylthiobutanoate obtained in the above mentioned step in a 2-liter flask equipped with a stirrer, a thermometer and a distilling tube were added 432 g of water and 8 g of "Amberlyst 15" (product of Rohm & Haas, Co.). The mixture was heated at 95° C. for 5 hours, while distilling off the resulting methanol. Amount of methanol thus distilled was 30.2 g.

As the result of analysis of the reaction mixture and the distillate, the conversion rate of methyl 2-hydroxy-4-methylthiobutanoate was 98.8%, the selectivity for 2-hydroxy-4-methylthiobutanoic acid was 97.1% and the selectivity for methanol was 98.8%.

After filtering off the catalyst from the reaction mixture, the filtrate was concentrated under reduced pressure to give 127 g of 88 weight % aqueous solution of 2-hydroxy-4-methylthiobutanoic acid (112 g).

[Production of hydrogen cyanide by dehydration of formamide]

Alumina catalyst ["N-612" available from Nikki Kagaku Co., Ltd.] (50 g) was packed into a stainless steel reaction tube (28 mm diameter, 30 cm length), and formamide obtained in the step of production of methyl 2-hydroxy-4-methylthiobutanoate, and nitrogen as a diluent were supplied thereto at the rates of 0.67 g/min. and 50 ml/min. respectively. The resultant gas was bubbled through water to absorb hydrogen cyanide.

As,the result of analysis of the absorbed solution, the conversion rate of formamide was 97.4% and the selectivity for hydrogen cyanide was 93.3%.

Hydrogen cyanide was recovered from the absorbed solution in a conventional manner to be utilized as a reactant for production of 2-hydroxy-4-methylthiobutyronitrile.

[Production of methyl formate from methanol]

Copper nitrate (210 g) was dissolved in water (400 g) and the solution was heated at 70° C. Separately, in 100 g of water was dissolved 23 g of ammonium chromate, then the resulting solution was heated at 70° C. The solution of copper nitrate was added to the solution of ammonium chromate with stirring. To the mixed solution was added an aqueous solution of ammonia to adjust the pH value to 9.5. The resulting precipitate was filtrated, washed with water sufficiently, dried at 90° C. for one day and calcined at 450° C. The powder thus obtained was compression-molded into a column form of 3 mm (diameter)×3 mm (length) to give a catalyst.

The catalyst thus obtained (50 ml) was packed into a stainless steel reacting tube (28 mm diameter, 30 cm length) and hydrogen gas was supplied thereto at 200° C. at a space velocity of 5000 per hour for 8 hours to reduce the catalyst.

After the reduction of the catalyst was completed, methanol obtained in the step of the production of 2-hydroxy-4-methylthiobutanoic acid was supplied thereto at 180° C. at a space velocity of 2500 per hour.

As the result of analysis of the resulting gas, the conversion rate of methanol was 36.4% and the selectivity for methyl formate was 91.0%.

Methyl formate was recovered in a conventional manner to be utilized as a reactant for production of methyl 2-hydroxy-4-methylthiobutanoate.

I claim:

1. A process for producing 2-hydroxy-4-methylthiobutanoic acid which comprises (1) the first step of hydrating 2-hydroxy-4-methylthiobutyronitrile for the formation of 2-hydroxy-4-methylthiobutanamide, (2) the second step of reacting the 2-hydroxy-4-methylthiobutanamide obtained in said first step with methyl formate for the formation of methyl 2-hydroxy-4-methylthiobutanoate and formamide and (3) the third step of hydrolyzing the methyl 2-hydroxy-4-methylthiobutanoate obtained in said second step for the formation of 2-hydroxy-4-methylthiobutanoic acid and methanol.

2. The process for producing 2-hydroxy-4-methylthiobutanoic acid as claimed in claim 1 which further comprises a preliminary step of reacting acrolein with hydrogen cyanide and methanethiol for the formation of 2-hydroxy-4-methylthiobutyronitrile to be used as the reactant in the first step and wherein the formamide obtained in the second step is dehydrated for the formation of hydrogen cyanide for the use thereof in said preliminary step.

3. The process for producing 2-hydroxy-4methylthiobutanoic acid as claimed in claim 1, wherein the methanol obtained in the third step is converted to methyl formate and the thus-obtained methyl formate is used in the second step.

4. The process for producing 2-hydroxy-4-methylthiobutanoic acid as claimed in claim 1 which further comprises a preliminary step of reacting acrolein with hydrogen cyanide and methanethiol for the formation of 2-hydroxy-4-methylthiobutyronitrile to be used as the reactant in the first step and wherein the formamide obtained in the second step is dehydrated for the formation of hydrogen cyanide for the use thereof in said preliminary step and the methanol obtained in the third step is converted to methyl formate for the use thereof in the second step.

5. The process for producing 2-hydroxy-4-methylthiobutanoic acid as claimed in claim 2, wherein the dehydration of formamide is carried out at 200° to 600° C. in the presence of a solid catalyst.

6. The process for producing 2-hydroxy-4-methylthiobutanoic acid as claimed in claim 3, wherein the conversion of methanol to methyl formate is carried out in the manner of dehydration using a solid catalyst or carbonylation with carbon monoxide.

7. The process for producing 2-hydroxy-4-methylthiobutanoic acid as claimed in claim 1, wherein the hydrolysis reaction in the third step is carried out in the presence of an acid catalyst.

8. The process for producing 2-hydroxy-4-methylthiobutanoic acid as claimed in claim 7, wherein a cation exchange resin is used as the acid catalyst.

9. The process for producing 2-hydroxy-4-methylthiobutanoic acid as claimed in claim 8, wherein a porous, strongly acidic cation exchange resin is used as the cation exchange resin.

10. The process for producing 2-hydroxy-4-methylthiobutanoic acid as claimed in claim 4, wherein the hydration reaction in the first step is carried out in the presence of a weak base or a metal oxide as a catalyst, the reaction in the second step is carried out in the presence of a metal salt or metal alkoxide as a catalyst, and the hydrolysis reaction in the third step is carried out in the presence of an acid catalyst.

11. A process for producing 2-hydroxy-4-methylthiobutanoic acid which comprises a step of reacting acrolein with hydrogen cyanide and methanethiol for the formation of 2-hydroxy-4-methylthiobutyronitrile; a step of hydrating said 2-hydroxy-4-methylthiobutyronitrile for the formation of 2-hydroxy-4-methylthiobutanamide; a step of reacting said 2-hydroxy-4-methylthiobutanamide with methyl formate for the formation of methyl 2-hydroxy-4-methylthiobutanoate and formamide; a step of hydrolyzing said methyl 2-hydroxy-4-methylthiobutanoate in the presence of an acid catalyst for the formation of 2-hydroxy-4-methylthiobutanoic acid and methanol; a step of dehydrating said formamide for the formation of hydrogen cyanide for the use thereof in said step for the formation of 2-hydroxy-4-methylthiobutyronitrile; and a step of conversion of said methanol to methyl formate for the use thereof in said step for the formation of methyl 2-hydroxy-4-methylthiobutanoate and formamide by dehydrogenation using a solid catalyst or carbonylation with carbon monoxide.

12. The process for producing 2-hydroxy-4-methylthiobutanoic acid as claimed in claim 11, wherein the hydration of 2-hydroxy-4-methylthiobutyronitrile is carried out in the presence of a weak base or a metal oxide as a catalyst, the reaction of 2-hydroxy-4-methylthiobutanamide with methyl formate is carried out in the presence of a metal salt or metal alkoxide as a catalyst, and the dehydration of formamide is carried out in the presence of a dehydration catalyst.

13. The process for producing 2-hydroxy-4-methylthiobutanoic acid as claimed in claim 11, wherein the hydration of 2-hydroxy-4-methylthiobutyronitrile is carried out in the presence of a weak base or a metal oxide as a catalyst, the reaction of 2-hydroxy-4-methylthiobutanamide with methyl formate is carried out in the presence of a metal salt or metal alkoxide as a catalyst, the hydrolysis of methyl 2-hydroxy-4-methylthiobutanoate is carried out in the presence of a cation exchange resin, the dehydration of formamide is carried out in the presence of a dehydration catalyst, and the conversion of methanol to methyl formate is performed by dehydrogenation using a dehydrogenation solid catalyst.

* * * * *